US009480691B1

(12) United States Patent
Roth

(10) Patent No.: US 9,480,691 B1
(45) Date of Patent: *Nov. 1, 2016

(54) TOPICAL LIQUID CONTAINING REFINED PEANUT OIL FOR TREATING SKIN PROLIFERATION OR INFLAMMATION DISORDERS

(75) Inventor: Jerry Roth, Sanford, FL (US)

(73) Assignee: Hill Dermaceuticals, Inc., Sanford, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/407,808

(22) Filed: Feb. 29, 2012

Related U.S. Application Data

(63) Continuation of application No. 12/646,929, filed on Dec. 23, 2009, now abandoned.

(60) Provisional application No. 61/145,880, filed on Jan. 20, 2009.

(51) Int. Cl.
*A61K 31/573* (2006.01)
*A61K 47/06* (2006.01)
*A61K 47/44* (2006.01)
*A61K 8/37* (2006.01)
*A61K 8/86* (2006.01)

(52) U.S. Cl.
CPC ............... *A61K 31/573* (2013.01); *A61K 8/37* (2013.01); *A61K 8/86* (2013.01); *A61K 47/06* (2013.01); *A61K 47/44* (2013.01)

(58) Field of Classification Search
None
See application file for complete search history.

(56) References Cited

U.S. PATENT DOCUMENTS

| 4,992,478 | A | * | 2/1991 | Geria | 514/782 |
|---|---|---|---|---|---|
| 5,645,854 | A | | 7/1997 | Masiz | |
| 5,811,111 | A | | 9/1998 | McAtee et al. | |
| 5,851,543 | A | | 12/1998 | Korb et al. | |
| 6,013,271 | A | | 1/2000 | Doughty et al. | |
| 6,126,920 | A | * | 10/2000 | Jones et al. | 424/45 |
| 6,267,985 | B1 | | 7/2001 | Chen et al. | |
| 2003/0031727 | A1 | | 2/2003 | Hahn et al. | |
| 2004/0009130 | A1 | * | 1/2004 | Detore et al. | 424/59 |

FOREIGN PATENT DOCUMENTS

WO WO-2005/009406 A1 2/2005

OTHER PUBLICATIONS

Liebel et al., Anti-inflammatory and anti-itch activity of sertaconazole nitrate, Arch Dermatol Res. Sep. 2006;298(4):191-9, printed from http://www.ncbi.nlm.nih.gov/pubmed/16868738, Abstract only, 2 pages.*
Ziogas et al., Effects of sterol biosynthesis inhibitors on mitosis, Pesticide Biochemistry and Physiology, vol. 37, issue 3, Jul. 1990 254-265, printed from http://www.sciencedirect.com/science/article/pii/004835759090132L, Abstract only, 2 pages.*
Hill Pharmaceuticals, Derma-Smoothe/FS®, 1999 FDA Label, 1999, obtained from http://www.accessdata.fda.gov/drugsatfda_docs/label/1999/19425s15lbl.pdf, 8 pages.*
Cevc, Drug delivery across the skin, Expert Opinion on Investigational Drugs Dec. 1997, vol. 6, No. 12, pp. 1887-1937.*
Kim et al., Evaluation of skin surface hydration in Korean psoriasis patients: a possible factor influencing psoriasis, Clin Exp Dermatol. Mar. 2002;27(2):147-52, printed from http://www.ncbi.nlm.nih.gov/pubmed/11952709, Abstract only, 1 page.*
American Heritage Dictionary of the English Language, Mineral Oil, 2011, printed from http://search.credoreference.com/content/entry/hmdictenglang/mineral_oil/0?searchId=772a6098-d70d-11e4-b8d7-0aea1e3b2a47&result=3, 1 page.*
Gordon, The role of clobetasol propionate emollient 0.05% in the treatment of patients with dry, scaly, corticosteroid-responsive dermatoses, Clin Ther. Jan.-Feb. 1998;20(1):26-39, printed from http://www.ncbi.nlm.nih.gov/pubmed/9522102, 2 pages.*
Non-Final Office Action issued by the U.S. Patent & Trademark on Apr. 3, 2015 for U.S. Appl. No. 14/144,832, filed Dec. 31, 2013 (Inventor—Jerry Roth // Applicant—Hill Dermaceuticals, Inc.) (14 pages.)
Ammendment and Response to Non-Final Office Action filed on Oct. 5, 2015 for U.S. Appl. No. 14/144,832, filed Dec. 31, 2013 (Inventor—Jerry Roth // Applicant—Hill Dermaceuticals, Inc.) (10 pages).
Non-Final Office Action Issued by the U.S. patent & Trademark Office on Apr. 3, 2015 for U.S. Appl. No. 14/182,903, filed Feb. 18, 2014 (Inventor—Jerry Roth // Applicant—Hill Dermaceuticals, Inc.) (15 pages).
Amendment and Response to Non-Final Office Action filed on Oct. 5, 2015 for U.S. Appl. No. 14/182,903, filed Feb. 18, 2014 (Invetor—Jerry Roth // Applicant—Hill Dermaceuticals, Inc.) (11 pages).
Final Office Action issued by the U.S. Patent & Trademark Office on Feb. 4, 2016 for U.S. Appl. No. 14/182,903, filed Feb. 18, 2014 (Inventor—Jerry Roth // Applicant—Hill Dermaceuticals, Inc.) (21 pages).
Beltrani et al., Immunol Allergy Clin N Am 25:557-580, 2005.
Del Rosso & Friedlaznder, J. Am Acad Dermatol 53:S50-58, 2005, Corticosteroids: Options in the era of steroid-sparing therapy.
Gulliver & Eid, Immunol Allergy Clin N Am 25:541-555, 2005.
Hengge et al., J. Am. Acad. Dermatol. 54: 1-15, 2006.
Lack et al., "Factors Associated with the Development of Peanut Allergy in Childhood," New England Journal of Medicine 348:977-985, 2003.
Lever, British Medical Journal 313-299-300, 1996 Peanut and nut allergy.
Yawalkar et al., J. Am. Acad. Dermatol. 25:1137-1144, 1991.

* cited by examiner

*Primary Examiner* — Gigi Huang
(74) *Attorney, Agent, or Firm* — Ballard Spahr LLP

(57) ABSTRACT

A liquid medicament for use on skin, epithelium, epidermis, body surface and so on containing a refined peanut oil and, for example, at least one agent which minimizes cell growth, inflammation or both.

14 Claims, No Drawings

TOPICAL LIQUID CONTAINING REFINED PEANUT OIL FOR TREATING SKIN PROLIFERATION OR INFLAMMATION DISORDERS

FIELD OF THE INVENTION

The invention relates generally to liquid medicinal compositions comprising a refined peanut oil, such as an oil, rub, gel and the like, containing one or more of an antiproliferative agent, an agent that slows or halts cell growth, an anti-inflammatory agent and so on, such as, clobetasol propionate.

BACKGROUND OF THE INVENTION

Medicinal topical preparations can serve as drug delivery means. The vehicles thereof carry a pharmacologically active agent to the body, such as the skin, whether exposed or in an orifice or canal, or to other parts of the body by way of the skin, epidermis, epithelium and so on.

Certain skin disorders are believed to arise from inflammation or hyperproliferation of skin cells, such as, epidermal or dermal cells. Among such diseases are basal cell carcinoma, malignant melanoma, squamous cell carcinoma, actinic keratosis, Bowen's Disease, papilloma, seborrheic keratosis, eczema, allergic eczema, atopic dermatitis, ichthyosis and psoriasis.

In the case of psoriasis, a range of disorders associated therewith are known, such as, psoriasis vulgaris, guttate psoriasis, flexural psoriasis, erythrodermic psoriasis, generalized pustular psoriasis and localised pustular psoriasis.

Many of the disorders of interest are characterised by epidermal or dermal cell hyperproliferation, such as increased growth of keratinocytes. Such increased cell proliferation is associated with increased DNA synthesis, and that increased DNA synthesis can be a target for pharmacologic agents.

Eczema, also known as atopic dermatitis, relates to a variety of common skin diseases, which are characterized by itchy, red, flaking, weeping or oozing skin. Eczema is also known as skin contact allergy, seborrheic eczema, and dry skin eczema (winter itch).

Commonly used treatments for such skin disorders include local treatment with vitamin D derivatives. However, generally, Vitamin D is slow working and can cause temporary skin irritation.

Such dermatological conditions also can be treated with topical corticosteroids, which are known to have an anti-inflammatory activity, often acting at the level of the immune system. Corticosteroids also can impact carbohydrate and protein metabolism. Those conditions are commonly known as steroid-responsive dermatoses, skin disorders that improve on treatment with topical steroids.

Local treatment with steroids can be associated with thinning of the skin, easy bruising, telangiectasia, epidermal disturbances, rosacea, acne, hypertrichosis, hypopigmentation, stretch marks among other unwanted side effects. (Hengge et al., J Am Acad Dermatol 54:1-15, 2006; Del Rosso & Friedlander, J Am Acad Dermatol 53:S50-58, 2005; and Beltrani et al., Immunol Allergy Clin N Am 25:557-580, 2005) Furthermore, administration of steroids can result in a rebound phenomenon, an exaggerated body response to terminating steroid treatment.

In controlled clinical trials, various adverse reactions to steroid therapy commonly are observed, including local burning, pruritus, local dryness, local pain, hyperpigmentation around resolving plaque, irritation and atrophy. A clobetasol propionate spray is not recommended for use on individuals younger than 18 years of age, treatment should be limited to 2 consecutive weeks, the total dosage should not exceed 50 g (59 mL or 2 fl oz) per week, the spray should not be used on the face, or in the groin or axillae, and patients should use the spray only for the minimum period necessary to achieve desired results.

Of importance is the impact such topical steroids can have at remote sites in the body. For example, clobetasol propionate is known to suppress the hypothalamus-pituitary-adrenal (HPA) axis at effective and prescribed doses. That can lead to reduced cortisol secretion resulting from a reduced amount of CRH. Abrupt withdrawal of exogenous steroids may precipitate an adrenal crisis. Gulliver & Eid, Immunol Allergy Clin N Am 25:541-555, 2005; Yawalkar et al., J Am Acad Dermatol 25:1137-1144, 1991.

Because of the impact of exogenous steroids on the pituitary, hypothalamus and adrenal glands, which can lead to range of systematic sequellae arising from the impact of hormones, such as, the adrenal hormones, on various tissues in the body, containing exogenous steroids at the site needed, such as the skin, is important to minimize unwanted systemic side effects.

Topical steroids commonly are divided into groups according to strength, see, for example, Hengge et al., supra. Very potent steroids (up to 600 times as potent as hydrocortisone) include clobetasol propionate and betamethasone dipropionate. Potent steroids (50-100 times as potent as hydrocortisone) include betamethasone valerate, diflucortolone valerate, hydrocortisone 17-butyrate, mometasone furoate and methylprednisolone aceponate. Moderate steroids (2-25 times as potent as hydrocortisone) include clobetasone butyrate and triamcinolone acetonide. The methods for assessing the strength of a steroid are known and are recognized by regulatory and international health care agencies, such as, the US FDA and WHO, see, also, Habif, Clinical Dermatology. 1990. Mosby. Inside of the front cover.

Thus, there remains a need in the art for a therapeutic product and approach that can contain and deliver one or more active agents or medicines using a vehicle with beneficial properties for use on keratinized skin or on mucosa. Such a liquid vehicle, for example, an oil, a thin gel, a spirit, a tincture, a suspension, a splash and the like would be one that can carry an effective pharmacologic agent for treating skin inflammation diseases with minimal adverse impact, and that has a non-drying, moisturizing and/or penetrating effect on human skin.

SUMMARY OF THE INVENTION

The invention provides a liquid composition for use on skin or in a body orifice containing an agent that reduces cell growth and/or inflammation, and a hypoallergenic or non-allergenic refined peanut oil, along with other optional ingredients, such as an emulsifier, a stabilizer and so on, as known in the art.

The invention provides for a means of delivering strong or potent pharmacologically active agents to skin, epidermis, epithelium and so on with a minimal side effect.

DETAILED DESCRIPTION OF THE INVENTION

A composition of the invention is in liquid form and therefore can be employed as an oil, a rub, a splash, an emulsion, a suspension, a liquid, an enema, a douche, drops and so on. Such compositions can be considered topical compositions as they are applied to skin, epidermis, epithelium, mucus membranes, body surfaces and so on, as known in the art. For the purposes of the instant invention, each of those terms are considered equivalents and use of one term, unless the context so indicates to the contrary, is considered equivalent to the other terms, specifically and generically. Liquid forms have the advantage of being easier to employ by non-professionals for instillation or application to epidermis and mucosa. Such forms also can provide for an even and extensive exposure of a pharmacologic agent to epidermis, body surfaces, mucosa and so on.

An active ingredient in the composition can include an agent that can be used to treat various skin disorders characterized by abnormal cell growth and/or inflammation, such as observed in eczema, psoriasis, dermatitis, seborrhea and so on. The active ingredient(s) is(are) suspended in a vehicle of interest comprising a refined peanut oil. The vehicle can contain other suitable oils, such as mineral oil, such as a light mineral oil.

The instant topical composition is one that carries superior and unexpected properties, such as excellent skin hydrating and penetrating properties, and providing a means for delivering a pharmacologic agent with reduced or minimal side effect, such as, minimal disruption of the HPA axis, obtained by the inclusion of a hypoallergenic, non-allergenic or refined peanut oil in the vehicle.

A pharmacologic agent of interest is one which is effective in slowing, minimizing and so on, abnormal cell growth and/or inflammation. Examples of such agents include antimitotic agents, anti-inflammatory agents, vitamins, steroids and so on. Thus, for example, corticosteroids, including naturally occurring and artificial or synthetic forms, can be used.

Corticosteroids, including halogenated corticosteroids, such as those that are fluorinated, that can be used in the topical preparations of interest generally are known, often as anti-inflammatory agents, and are commercially available. Examples include cortisone, hydrocortisone and derivatives thereof including cortodoxone, flucetonide, fludrocortisone acetate, flurandrenolone acetonide, medrysone; prednisone, prednisolone and derivatives thereof including amcinafal, amcinafide, betamethasone benzoate, valerate and dipropionate, chloroprednisone acetate, descinalone acetonide, desonide, dexamethasone, dichlorisone acetate, difluprednate, flucloronide, flumethasone, flunisolide acetate, fluocinolone acetonide, fluocinonide, fluocortolone, fluorometholone, fluperoline acetate, fluprednisolone valerate, meprednisone, methyl prednisolone, paramethasone acetate, prednisolomate, prednisolone acetate, butylacetate and phosphate sodium, triamcinolone acetonide, hexacetonide, diacetate, hydrocortisone butyrate, flumethasone pivalate, halcininide and clobetasol propionate.

Compositions containing peanut oil are a cause of nut allergy (Lever, British Medical Journal 313:299-300, 1996). A recent study revealed that infants sensitized to peanuts might have been exposed to peanut oil (Lack et al., New England Journal of Medicine 348:977-985, 2003). Yet, peanut oil can be found in certain compositions, such as in injectables, creams and ointments, where the oil serves as a reservoir of a drug or as an inert lipid carrier.

Thus, there remains no appreciation of employing peanut oil that is non-allergenic. Moreover, there is no appreciation of the skin hydrating and/or skin penetrating properties of including a non-allergenic, refined peanut oil in a topical formulation.

The refined peanut oil of interest is commercially available (Welch, Holme & Clark, Newark, N.J.). A refined peanut oil of interest is one that is suitable for pharmaceutical use and is substantially free of proteins, and particularly those proteins known to be allergenic in humans, such as the ara h glycoproteins. Thus, a peanut oil of interest is treated to deactivate, to remove the biological activity, and at the least, the immunogenicity of such allergenic proteins and thus essentially is hypoallergenic and preferably non-allergenic.

For example, a refined peanut oil of interest is a peanut oil that is treated with alkali (or other refining solution) and/or heat. Many peanut oil impurities, including the proteinaceous allergens, can be hydrated, and then separated. A water washing can be used to remove such impurities, the bulk of which often are removed in the form of soaps, with the proteins attached or associated with the soaps. Alternatively, proteins and the like which are water soluble, are removed by partitioning into the aqueous phase in such partitioning exercises.

The refined peanut oil of interest optionally then can be bleached to remove other impurities, such as colored compounds and other remaining impurities. Generally, the bleaching process involves adsorption onto a carrier, such as activated carbon or a silicate, such as a clay, such as bentonite. Generally, the refined oil is passed over a bed of adsorbent or the adsorbent is mixed in the oil and then removed.

The refined peanut oil of interest optionally then can be further treated with a steam distillation process, often under vacuum.

A refined peanut oil of interest can be exposed to all three of the above treatments, in the order of, for example but not limiting, refining, bleaching and then vacuum steam distillation.

A refined peanut oil of interest can be treated by other methods, the goal being to inactivate or to remove the proteinaceous peanut oil allergens.

Inactivation of the peanut oil allergens can be monitored using any of a variety of methods, for example, the tests available from Neogen (Lansing, Mich.). Antibody to the various ara h glycoproteins is commercially available or can be made practicing known immunology methods. Both polyclonal or monoclonal antibodies can be made and used. Current commonly used antibodies are polyclonal, being raised to a collection of peanut protein, and thus to a variety of allergens. The use of such antibodies for the detection of peanut allergens can rely on any of the known assay formats, such as an ELISA. Commercially available tests can detect as little as 2.5 parts per million (ppm) of peanut protein. Using an antibody directed to peanut proteins in an ELISA, the refined peanut oil of interest was found to contain less than 1 ppm of peanut protein. An alternative is to conduct peptide or amino acid analysis or sequencing of any proteins or protein fragments that may be present in the oil. Methods and materials for conducting peptide or amino acid analysis or sequencing are commercially available.

The composition of interest comprises a vehicle comprising refined peanut oil in an amount of at least 30%, at least 40%, at least 45%, at least 50% or more by volume. The composition can comprise essentially all refined peanut oil, aside from the active agent(s) and any other diluents, excipients and carriers that might be used as a design choice. Thus, for example, a composition of interest can include from about 30-95%, 30-90%, 30-85%, 30-80%, 30-75%, 30-70%, 30-65%, 30-60%, 30-55%, about 40-95%, 40-90%, 40-85%, 40-80%, 40-75%, 40-70%, 40-65%, 40-60%, 40-55%, about 45-95%, 45-90%, 45-85%, 45-80%, 45-75%, 45-70%, 45-65%, 45-60%, 45-55% and so on by volume of refined peanut oil. (The percentages herein relate to either by volume, weight per volume or by weight measurements, for the purposes of the instant invention, all are equivalent.) The liquid vehicle can comprise any of a variety of known fillers, excipients and diluents, aqueous or non-aqueous, as known in the art. For example, a suitable excipient is mineral oil, such as a light mineral oil.

The vehicle of interest can contain at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, and at least 94% or more by weight of refined peanut oil. Again, the percentages used herein apply either to a weight basis, weight per volume or a volume basis calculation. The properties of the final vehicle and the compatibility thereof with the one or more pharmaceutically active agents incorporated therein can determine the amount of refined peanut oil used.

Another oil can be used with the refined peanut oil of interest, so long as the oil is compatible with the other ingredients in the formulation and with the site of intended use. Suitable oils include a mineral oil or an oil containing a fatty acid ester of glycerol, such as a vegetable oil, such as castor oil, cotton seed oil, soybean oil, olive oil and so on.

As is known in the art, oils may be derived from animals, plants, nuts, petroleum etc. Those derived from animals, plants, seeds and nuts are similar to fats and consequently, can contain one or a significant number of polar acids and/or ester groups. Alternatively, oils derived from petroleum are usually aliphatic or aromatic hydrocarbons that are essentially free of polar substitution and therefore may be preferred for certain applications. It is preferable for the oils to be refined so as to be compatible with human tissue, and to be hypoallergenic or non-allergenic as well.

Other oil-based products that can be used include hydrocarbons such as lanolin or wool fats that are obtained from sheep wool and composed of fatty acids and cholesterol esters; and cetyl and stearyl alcohols, which are solid alcohols obtained by hydrogenation of their respective acids Amphophilic compounds such as soaps or salts of fatty acids, that may be acidic or basic depending on whether the lipophilic group is anionic or cationic, sulfated alcohols which are semi-synthetic substances and synthetic surface active agents are known in the art and can be used in the topical preparation of interest. Glycerine can be obtained from fats and, due to the hydrophobicity thereof, has the property of extracting water from the surface of the mucosa or denuded skin. Glycerin does not damage intact skin. Because glycerine has hydrophilic properties as well, glycerin is a useful humectant in a preparation of interest.

A solvent that can be used for an aqueous portion, if present, may be, for example, purified water, particularly distilled water for injection.

The formulation may contain various additives as appropriate, such as a buffer, an osmotic agent, a preservative, a surfactant or detergent, a skin penetrant, a lubricant, an emollient, an emulsifier, an antimicrobial, such as an antibiotic, an antifungal, an antiviral and so on, a bulking agent, a chelating agent and the like.

Examples of a buffer include a phosphate buffer, a carbonate buffer, a borate buffer, a citrate buffer, a tartrate buffer, an acetate buffer, amino acid(s) and the like.

Examples of an osmotic agent include sugars, such as sorbitol, glucose, mannitol and the like, polyhydric alcohols such as glycerol, propylene glycol (PEG) and the like, salts such as sodium chloride and the like, and other osmotic agents as known in the art.

Examples of surfactants and detergents include ionic surfactants, nonionic surfactants, polyoxyethyleneoxystearic acid triglyceride, PEG, alcoholic lipids, such as, alcoholic fatty acids, such as, for example, isopropyl myristate, PEG ethers of fatty acid alcohols, such as, oleyl alcohols, polyoxyethylene hydrogenated castor oil and the like. Other surfactants include polyoxyethylenesorbitan fatty acid esters, such as polyoxyethylenesorbitan monooleates, polyoxyethylenesorbitan monolaurates, polyoxyethylenesorbitan monopalmitates, polyoxyethylenesorbitan monostearates and the like. Examples of PEG-fatty acid ethers include PEG oleyl alcohol ethers. Suitable examples, include compounds known as Oleths, such as Oleth 2, Oleth 3, Oleth 4, Oleth 5, Oleth 6 and so on, where the number in the name represents the average number of ethylene oxide units.

Examples of amphoteric surfactants useful in the compositions of the instant invention include those disclosed in McCutcheon's, "Detergents and Emulsifiers", North American edition (1986) and McCutcheon's, "Functional Materials", North American Edition (1992); both of which are incorporated by reference herein in their entirety. Surfactants that can used include the betaines, sultaines and hydroxysultaines. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine, lauryl bis-(2-hydroxyethyl) carboxymethyl betaine, steryl bis-(2-hydroxypropyl) carboxymethyl betaine, oleyl dimethyl gamma-carboxypropyl betaine, lauryl bis-(2-hydroxypropyl)α-carboxyethyl betaine, coco dimethyl sulfopropyl betaine, stearyl dimethyl sulfopropyl betaine, stearyl betaine, lauryl dimethyl sulfoethyl betaine, lauryl bis-(2-hydroxyethyl) sulfopropyl betaine, and amidobetaines and amidosulfobetaines, oleyl betaine, and cocamidopropyl betaine). Examples of sultaines and hydroxysultaines include cocamidopropyl hydroxysultaine. Examples of other amphoteric surfactants are alkyliminoacetates, iminodialkanoates and aminoalkanoates. Other examples of emulsifiers include the Oleth compounds.

Examples of anionic surfactants also are disclosed in McCutcheon's (1986) and McCutcheon's (1992), supra. Examples include the alkoyl isethionates, and the alkyl and alkyl ether sulfates, such as, ammonium cocoyl isethionate, sodium cocoyl isethionate, sodium lauroyl isethionate, sodium stearoyl isethionate and mixtures thereof, the sarcosinates, such as sodium lauroyl sarcosinate, sodium cocoyl sarcosinate, and ammonium lauroyl sarcosinate, sodium lauryl sulfate, ammonium lauryl sulfate, ammonium cetyl sulfate, sodium cetyl sulfate, sodium stearyl sulfate, ammonium cocoyl isethionate, sodium lauroyl isethionate, sodium lauroyl sarcosinate, and mixtures thereof.

Examples of a bulking agent include polyvinylpyrrolidone, hydroxyethylcellulose, hydroxypropylcellulose, methylcellulose, hydroxypropylmethylcellulose, carboxymethylcellulose, salts thereof and the like.

Examples of a chelating agent include EDTA and citric acid.

The compositions of the instant invention can comprise a wide range of components as known in the art. The "CTFA Cosmetic Ingredient Handbook", Second Edition, 1992, which is incorporated by reference herein in its entirety, describes a wide variety of cosmetic and pharmaceutical ingredients commonly used in the skin care industry, which are suitable for use in the compositions of the instant invention. Reference also can be made to U.S. Pat. Nos. 6,013,271; 6,267,985; 4,992,478; 5,645,854; 5,811,111; and 5,851,543. Examples of functional classes of ingredients are, to include and in addition to that disclosed hereinabove, absorbents, abrasives, anti-acne agents, anticaking agents, antifoaming agents, antimicrobial agents, antioxidants, binders, biological additives, buffering agents, such as sodium hydroxide, sodium citrate and EDTA, bulking agents, chelating agents, chemical additives, colorants, cosmetic astringents, cosmetic biocides, denaturants, dispersants, deodorants, lubricants, drug astringents, external analgesics, fragrance components, such as menthol, moisturizers, flavorants, humectants, thickeners, such as carboxymethylcellulose, opacifying agents, platicizers, preservatives, such as dichlorobenzyl alcohol, benzoic acid, methylparaben and phenyl, propellants, reducing agents, skin bleaching agents, opacifiers, such as zinc oxide, magnesium aluminum silicate and titanium dioxide, skin-conditioning agents (emollients and humectants), skin protectants, solvents, foam boosters, hydrotropes, solubilizing agents, suspending agents (nonsurfactant), gelling agents, such as petrolatum and mineral wax, sunscreen agents, ultraviolet light absorbers, and viscosity increasing agents (aqueous and nonaqueous). Examples of emollients include isopropyl myristate and the Oleths.

In addition, the topical carrier may include a penetration enhancer defined as a material that increases the permeability of the skin to one or more active agents so as to enhance permeability of the one or more active agents, such as dimethylsulfoxide, dimethyl formamide, dimethylacetamide, isopropyl myristate, decylmethylsulfoxide and polyethylene glycols.

Other materials that may be used in a topical preparation of interest include liquid alcohols, liquid glycols, liquid polyalkylene glycols, liquid esters, liquid amides, liquid protein hydrosylates, liquid alkylated protein hydrosylates, liquid lanolin and lanolin derivatives, and other like materials, that if not liquid, are soluble in a vehicle of interest or are used in an amount that is suspensible or usable with a vehicle of interest without reducing the flowable properties thereof. Particular examples include monohydric and polyhydric alcohols, e.g., ethanol, isopropanol, glycerol, sorbitol, 2-methoxyethanol, diethylene glycol, ethylene glycol, hexylene glycol, mannitol, cetyl alcohol and propylene glycol; ethers, such as diethyl or dipropyl ether; polyethylene glycols and methoxypolyoxyethylenes; carbowaxes having molecular weights ranging from 200 to 20,000; polyoxyethylene glycerols; polyoxyethylene; sorbitols; and stearoyl diacetin. The topical carriers can include an oil, a lipid, an alcohol and water so as to accommodate lipophilic and hydrophilic components.

A wide variety of antimetabolites, alkylating agents, antimitotic agents, antineoplastic agents, cytostatic agents, agents which impact cell growth, may be used in the medicament of interest. One or more of such active agents can be used in a preparation of interest. Examples include alkylating agents, enzyme inhibitors, proliferation inhibitors, DNA synthesis inhibitors, lytic agents, DNA intercalators, antimetabolites, steroids and the like. Illustrative agents include naturally occurring steroids, synthetic or artificial steroids, paclitaxel, ionomycin, etoposide, nitrosoureas such as carmustine, doxorubicin, daunorubicin, actinomycin D, meclorethamine, busulfan, chlorambucil, cactinomycin, carzinophilin, chlornaphazine, 6-chloropurine, azathioprine, fluorouracil, hydroxyurea, thioquanine, campothecin, mitomycin, lomustine, semustine, cantharidin, camptothecin, carboplatin, ricin, *pseudomonas* exotoxin, interferons, interleukins, TNF, vincristine, methchlorethamine, plicamycin, nitracine, nitoxantrone, methotrexate, nogalamycin, streptonigrin, streptozocin, tegafur, tetramin, testolactone, demecolcine and dactinomycin. Other compounds that can be used include cytophamide, cyclosporin, amsacrine, biantrene hydrochloride, camostat mesylate, campothecin, enocitabine, etoposide, epirubicin hydrochloride, fludarabine phosphate, flutamide, fotemustine, idarubicin hydrochloride, ionomycin, onidamine, mitoxantrone hydrochloride, nilutamide, paclitaxel, pirarubicin, toremifene, vinorelbine, didemnin, bactracyclin, mitoquidone, penclomedine, phenazinomycin, U-73975, saintopin, 9-aminocamptothecin, amonafide, merbarone and the like. Additional agents that can be used include mitomycin C, cisplatin, mechlorethamine, pyrazine diazohydroxide, fumagillin, rhyzoxin, dynemicin A, chlorambucil, semustine and the like.

Optionally, the composition also can contain an additional active agent for a different function or purpose. Hence, a composition of interest also can contain a keratolytic agent, including salicylic acid, derivatives of salicylic acid such as 5-octanoyl salicylic acid, and resorcinol; retinoids such as retinoic acid and derivatives thereof (e.g., cis and trans); sulfur-containing D and L amino acids and derivatives and salts thereof, particularly N-acetyl derivatives, such as N-acetyl-L-cysteine; lipoic acid; antibiotics and antimicrobials, such as benzoyl peroxide, actopirox, tetracycline, trichlorobanilide, azelaic acid, phenoxyethanol, phenoxypropanol, phenoxyisopropanol, ethyl acetate, clindamycin and meclocycline; sebostats such as flavonoids; and bile salts such as scymnol sulfate and derivatives thereof, deoxycholate and cholate.

Examples of antiwrinkle and antiskin atrophy actives that can be used in the topical preparations of interest include retinoic acid and derivatives; retinol; retinyl esters; salicylic acid and derivatives thereof; sulfur-containing D and L amino acids and their derivatives and salts, particularly the N-acetyl derivatives, thiols, e.g. ethane thiol; alpha-hydroxy acids, e.g. glycolic acid, and lactic acid; phytic acid, lipoic acid; lysophosphatidic acid, and skin peel agents, e.g., phenol.

Examples of non-steroidal anti-inflammatories that can be used in the instant invention include propionic acid derivatives; acetic acid derivatives; fenamic acid derivatives; biphenylcarboxylic acid derivatives; and oxicams, and include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, microprofen, tioxaprofen, suprofen, alminoprofen, tiaprofenic acid, fluprofen and bucloxis acid.

Examples of topical anesthetic drugs that can be used in the topical preparation of interest include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

The instant vehicle can contain one or more other pharmaceutically active agents for topical use, for example, vitamins, such as A, D, E or K, hormones, antimicrobials, such as antibacterials, antivirals, antifungals and the like, as known in the art or as taught herein. The amount of the additional active agent is as known in the art or can be determined empirically as known in the art.

Some medicaments, pharmaceuticals and drugs that can be used herein are those which previously may not have been amenable to general dermatologic use for any of a variety of reasons, such as those that are irritating to the skin or have other debilitating effects or unwanted side effects. For example, clobetasol propionate is a potent corticosteroid. However, that synthetic steroid can have undesirable side effects. The instant liquid vehicle overcomes those hurdles.

The refined peanut oil-containing formulations of interest can overcome or mitigate those side effects. The formulation of interest has unexpected and beneficial skin penetrating or, when an aqueous medium is present, hydrating property, provided, in part, by a refined peanut oil. The formulations of interest enhance rapid intradermal and transdermal penetration of the pharmacologically active agent or agents into the skin where the active agent is needed, may enhance residence time of same on the skin and minimize untoward side effects by minimizing system absorption of the pharmacologically active agent or agents.

In the various embodiments, the compositions of the invention are useful for application to any subject in need thereof. The subject can be any vertebrate, such as, a mammal, such as, a human. The composition is amenable to self-application. The amounts used are essentially as known in the art, although amounts can be modified based on empirical data and routine experimentation.

Hence, the active agent which reduces cell growth and/or inflammation can be used in an amount as known in the art. Thus, for example, clobetasol propionate can be used at 0.05% in commercially available products, such as a foam, cream, ointment and a spray. Thus, that concentration can be used in a formulation of interest, but without a side effect associated with that product.

The amounts used in the instant invention can be increased or decreased from the amount(s) used in current products because of the efficacious delivery by the instant vehicle and the property of the vehicle to buffer, or to mitigate an untoward side effect of certain active agents. Thus, because the instant vehicle minimizes a side effect, for example, the amount of clobetasol propionate can be increased to about 0.055%, about 0.06%, about 0.65%, about 0.7% or more and so on. Also, because the instant vehicle is effective in delivery, the amount of active agent can be decreased. Thus, in the case of clobetasol propionate the amount can be less than 0.05%, and can be decreased to about 0.0475%, to about 0.045%, to about 0.425% or less and so on.

The liquid of interest can be found in any of the known forms, as detailed hereinabove, and as known in the pharmaceutical and consumer drug product arts.

The liquid composition of interest can be delivered by any of the known means for delivering of such compositions, such as a dropper, a tube dispenser with a plunger, a nozzled bottle, an applicator, by hand and so on.

Other features, objects, and advantages of the invention will be apparent from the description. In the specification, the singular forms include plural references unless the context clearly dictates otherwise. Unless defined otherwise, all technical and scientific terms used herein have the same meaning as commonly understood by one of ordinary skill in the art to which this invention belongs.

The following example is presented to more fully illustrate the invention.

The example should in no way be construed as limiting the scope of the invention, as defined by the appended claims.

Clobetasol propionate (11β,16β)-21-chloro-9-fluoro-11-hydroxy-16-methyl-17-(1-oxo-propoxy)pregna-1,4-diene,3,10-dione) is obtained from Sicor S.R.L. (Milan, Italy). Refined peanut oil (final amount, 51.075% v/v) is charged into a mixer. Under mixing, mineral oil (final amount, 42% v/v) is added to the vessel, and then Oleth-2 (final amount, 3.125% v/v) is added, then isopropyl myristate (final amount, 3.75% v/v) is added and finally 0.05% w/v of clobetasol propionate is added to the mixer. Once the clobetasol propionate is dissolved, the mixture is aliquoted (about 120 ml) into 4 oz. white, opaque PVC bottles with white phenolic screw caps.

Patients with at least 20% total body surface area of psoriasis are selected for the study. A critical endpoint of the study is to assess the impact, if any, of the clobetasol propionate oil of interest on the HPA axis. Patients treat themselves twice a day for 14 days. Blood is drawn to determine cortisol levels using a standard test, before and 30 minutes after Cortrosyn (ACTH-derived corticotrophin molecule) stimulation at day 0 and day 15. Each patient must have a normally functioning HPA axis as revealed by an 8 AM plasma cortisol level of at least 5 µg/100 dl prior to the study and a response to the corticotrophin of at least 18 µg/100 dl cortisol 30 minutes after the IM or IV injection of the cortisol stimulant. The oil is applied to non-occluded skin as a thin film and spread gently over the lesion. Treated areas are not covered. If the psoriatic lesion clears, treatment is terminated.

Adverse events are limited and of lesser intensity than observed with the commercially available forms, such as a spray and a foam. No impact on the HPA axis is observed, as compared to the impacts observed with the commercially available forms. While not wanting to be bound by any theory, it is believed the reduced systemic adverse effects may result by the lateral migration and diffusion of the pharmacologic agent about and into the skin and those areas surrounding the site of treatment and an enhanced movement of the agents) into the skin cells rather than into the circulation.

The foregoing description has been presented only for the purposes of illustration and is not intended to limit the invention to the precise form disclosed.

All patents and publications cited in this specification are incorporated by reference herein in entirety.

The invention claimed is:

1. A topical oil composition consisting essentially of about 45% to 55% by volume refined peanut oil that contains less than 1 ppm of peanut protein, about 0.045% to 0.055% weight by volume clobetasol propionate; mineral oil; Oleth 2; and isopropyl myristate; wherein the composition does not suppress the hypothalamic-pituitary-adrenal axis when applied twice a day for 14 days on patients with psoriasis on at least 20% of the total body surface area.

2. The topical composition of claim 1, wherein the refined peanut oil is non-allergenic.

3. The topical composition of claim 1, wherein the refined peanut oil is substantially free of proteinaceous allergens.

4. The topical composition of claim 1, wherein the refined peanut oil is a peanut oil that has been treated with an alkali refining solution.

5. The topical composition of claim 1, wherein the refined peanut oil is a peanut oil that has been treated by an aqueous partitioning.

6. The topical composition of claim 1, wherein the refined peanut oil is a peanut oil that has been heat treated.

7. The topical composition of claim 1, wherein the refined peanut oil is a peanut oil that has been treated with a steam distillation process.

8. A topical oil composition consisting essentially of about 45% to 55% by volume refined peanut oil that contains less than 1 ppm of peanut protein, about 0.045% to 0.055% weight by volume clobetasol propionate; a mineral oil; Oleth 2; isopropyl myristate, and a fragrance component; wherein the composition does not suppress the hypothalamic-pituitary-adrenal axis when applied twice a day for 14 days on patients with psoriasis on at least 20% of the total body surface area.

9. The topical composition of claim 8, wherein the refined peanut oil is non-allergenic.

10. The topical composition of claim 8, wherein the refined peanut oil is substantially free of proteinaceous allergens.

11. The topical composition of claim 8, wherein the refined peanut oil is a peanut oil that has been treated with an alkali refining solution.

12. The topical composition of claim 8, wherein the refined peanut oil is a peanut oil that has been treated by an aqueous partitioning.

13. The topical composition of claim 8, wherein the refined peanut oil is a peanut oil that has been heat treated.

14. The topical composition of claim 8, wherein the refined peanut oil is a peanut oil that has been treated with a steam distillation process.

* * * * *